United States Patent [19]

Glassman

[11] Patent Number: 5,047,024

[45] Date of Patent: Sep. 10, 1991

[54] TAMPON CONSTRUCTION

[76] Inventor: Jacob A. Glassman, 1680 Michigan Ave., Miami Beach, Fla. 33139

[21] Appl. No.: 455,789

[22] Filed: Jan. 2, 1990

Related U.S. Application Data

[63] Continuation-in-part of Ser. No. 400,449, Aug. 30, 1989, abandoned.

[51] Int. Cl.[5] .............................................. A61F 13/50
[52] U.S. Cl. .................................. 604/380; 604/379; 604/378; 604/385.1
[58] Field of Search ...................... 604/379, 380, 385.1, 604/378

[56] References Cited

U.S. PATENT DOCUMENTS

| | | | |
|---|---|---|---|
| 2,771,882 | 11/1956 | Leupold | 604/385.1 |
| 3,359,981 | 12/1967 | Hochstrasser | 604/379 X |
| 3,369,544 | 2/1968 | Crockford | 604/385.1 X |
| 3,572,341 | 3/1971 | Glassman | 604/379 X |
| 3,854,481 | 12/1974 | Messing | 604/380 |
| 4,175,561 | 11/1979 | Hirschman | 604/385.1 |
| 4,335,720 | 6/1982 | Glassman | 604/379 |
| 4,361,151 | 11/1982 | Fitzgerald | 604/378 X |
| 4,627,849 | 12/1986 | Walton et al. | 604/379 |

Primary Examiner—Randall L. Green
Assistant Examiner—David H. Willse
Attorney, Agent, or Firm—Richard M. Saccocio

[57] ABSTRACT

The present invention provides an improved tampon construction for more efficient absorption of menstrual fluids. The tampon originates as a rectangularly-shaped wad of absorptive material which is twice folded over onto itself in different planes so as to provide twice as much absorptive material in the upper half as compared to the lower half thereof. The twice-folded material is then subjected to pressure which forms the same into a cylindrical shape. Thereafter, a plurality of slits emanating radially from the center thereof is provided at the top of the cylindrical shape while a plurality of axial grooves are provided along the cylindrical body thereof. The folded construction, in addition to the slits and grooves, provides for efficient menstrual fluid absorption by the tampon even in the event that it is misplaced within the vaginal canal. The inventive tampon readily absorbs menstrual fluids and expands by flowering of the upper end so as to adapt its shape to that of the vaginal canal and thereby prevent leakage of menstrual fluids past the tampon.

16 Claims, 3 Drawing Sheets

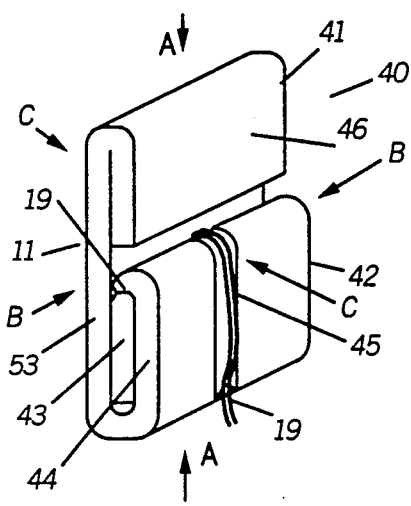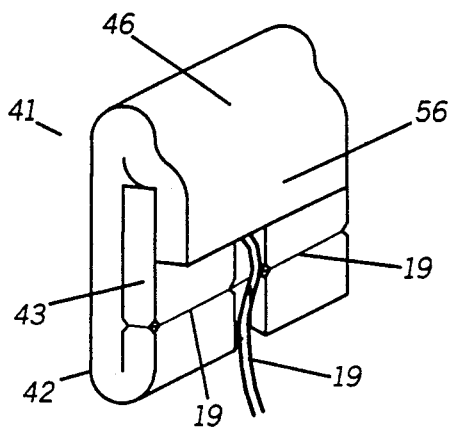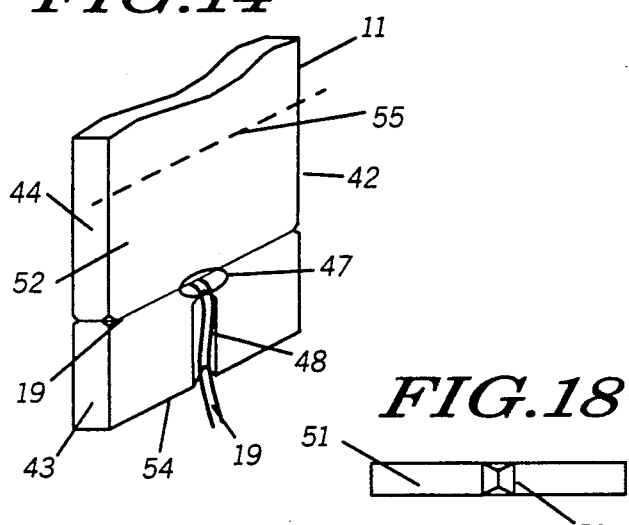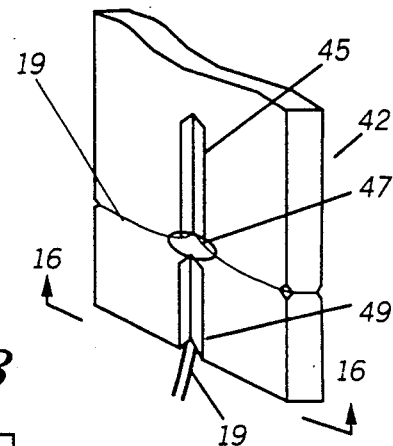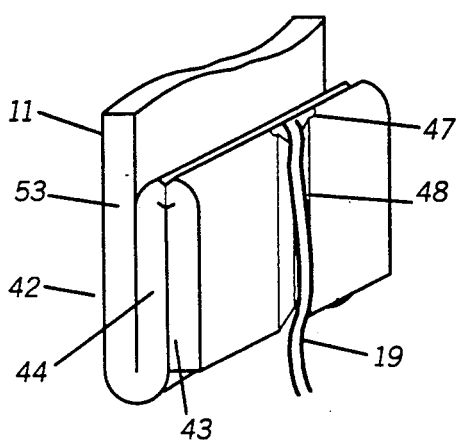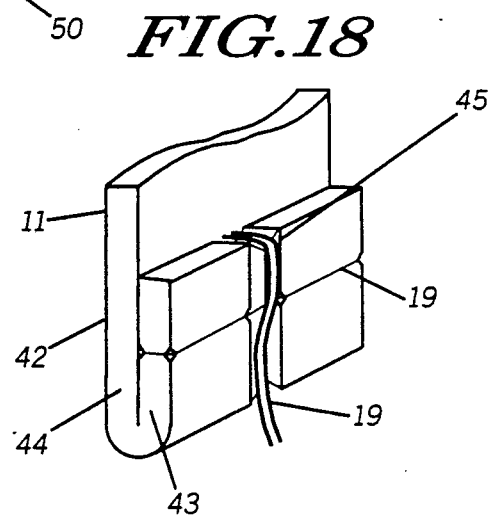

TAMPON CONSTRUCTION

This application is a continuation-in-part of application Ser. No. 07/400,449, filed Aug. 30, 1989, now abandoned.

BACKGROUND OF THE INVENTION

1. Field of the Invention

This invention pertains in general to the field of menstrual fluid absorbable apparatus and in particular to the field of an improved tampon construction for internally absorbing menstrual fluid.

2. Description of the Prior Art

Tampons, which are insertable within the vaginal canal of a female, are in extensive use today because of the convenience provided by such insertable devices. The prior art tampons typically comprise a wad of absorbable material, such as cotton or rayon, folded once along the length thereof and approximately three times along the width thereof, and thereafter compressed into a cylindrical shape for subsequent use. A cord or a string is typically attached to the wadded pad of absorbent material to facilitate the removal thereof following its use.

The typical prior art tampon substantially depends upon the naturally absorbent characteristics of the material from which the tampon is made to absorb the menstrual fluid. The folded-over portions of a tampon do not necessarily serve to aid in the absorption of the menstrual fluid because such folded-over portions are thereafter compressed by forming the wad of material into a cylindrical shape. Thus, when a tampon is inserted, the folded-over portions stay closed within the body cavity. Therefore, the only surfaces available for the absorption of the menstrual fluid comprise the cylindrical surface as well as the top surface of the tampon. The cylindrical surface is a very poor absorber of fluids due to its compressed nature and the arrangement of the fibers therein. Thus, as a practical matter, only the top surface is available for absorbing the menstrual fluid.

In preparing the tampon for use, the user must insert the same into the vaginal canal and push it upward so that hopefully the top end of the tampon is directly in line with the os of the cervix which, of course, is the site of the flow of the menstrual fluid. More often than not, the user pushes the tampon up too far in the vaginal canal such that the end thereof passes the os of the cervix and positions itself therebehind and into one of the spaces or fornices behind or to the sides of the cervix. Unfortunately, because the menstrual fluid strikes such a positioned tampon generally in the upper or middle one-third of the cylindrical area, the tampon is not being used in its most effective manner. Prior art tampons are designed such that maximum absorption is obtained when the menstrual fluid strikes the top surface of the cylindrical shape of the tampon. Because the menstrual fluid is not readily absorbed by the cylindrical surface of the tampon, the tampon fails to flower or open up and the effectiveness of the continued absorptive capability of the tampon is either reduced or lost. Thus, the farther away from the apex of the present day tampon that the menstrual fluid strikes the body of the tampon, the less efficiency in absorption can be expected. Moreover, such a condition concomitantly results in strike-through or leakage of the menstrual fluid from the vagina. Needless to say, the latter-mentioned occurrence is unacceptable.

Accordingly, a primary object of the present invention is to provide a tampon which readily absorbs fluids regardless of the position of the tampon within the vaginal canal.

Another object of the present invention is to provide a tampon which is effective in absorbing fluids from the top surface thereof or equally as well from any portion of the cylindrical surface thereof.

Another object of the present invention is to provide a tampon that when struck by menstrual fluid on its sides, it will then concomitantly cause the top side of the tampon to open up or "flower."

Another object of the present invention is to provide a tampon that when struck by the menstrual fluid on any of its sides or at any level, will then concomitantly cause the top side of the tampon to open up or "flower."

Further, prior art tampons tend to lengthen when being used; but, because of the natural compressive pressure exerted by the walls of the vagina, a cylindrically-shaped tampon remains cylindrical during use and, therefore, does not generally increase in diameter during use. This inability to overcome the pressure exerted by the vagina, which is radial because of the dry shape of the tampon, limits the absorptive ability of such tampons. This is evidenced by the shape of the prior art tampons after use.

Another aspect of the prior art tampons is that the absorption capabilities of the same depend entirely upon the ability of a fully compressed, usually cylindrically shaped, tampon to absorb fluids. The fully compressed shape is necessary for insertion purposes but tends to act against the ability of the tampon to achieve full capability of its absorptive characteristics.

Accordingly, a further object of the present invention is to provide a tampon which can be expanded or decompressed after being inserted and when dry so as to improve its ability to absorb menstrual fluids.

Another object of the present invention is to provide a tampon which can be shaped into a somewhat flattened shape after being inserted and when dry.

Another object of the present invention is to provide a tampon which improves absorption in a transverse direction notwithstanding the compressive pressure exerted by the wall of the vagina.

The above-stated objects as well as others objects which although not specifically stated, but are intended to be included within the scope of the present invention, are accomplished by the present invention and will become apparent from the hereinafter set forth Detailed Description of the Invention, Drawings, and the Claims appended herewith.

SUMMARY OF THE INVENTION

The present invention accomplishes the above-stated objectives as well as others, which comprises an improved tampon construction and method for making the same.

A rectangularly-shaped piece of absorbent material, such as cotton or rayon, is first folded over from the top to approximately the half-way point of the bottom portion. Then, the folded-over material is folded over on itself along a longitudinal line such that the top portion thereof contains approximately twice the volume of material as the bottom portion thereof. The folded-over material is then compressed by means of a die or other appropriate device into a cylindrical shape resulting in a configuration of a solid, circular cylinder of approximately two inches high and five-eighths of an inch in diameter. Naturally, the top one-half portion of the tampon is compressed more than the bottom half due to the extra volume of material in the top half thereof. During this operation, a convenience string is appropriately attached to the body of the tampon. Following compression, the upper portion of the upper half of the tampon is slit on at least three diametrical planes across the top of the cylinder and down along the axial length of the cylinder for approximately one-third of the length thereof. Further, a plurality of longitudinal grooves are provided within the cylindrical body of the tampon along the full length thereof.

In accordance with the construction of the tampon provided by this invention, the same is very effective in absorbing menstrual fluids regardless of the position of the tampon with respect to the os of the cervix or any of the fornices. The grooves and slits provided in the body of the tampon allow any menstrual fluid striking the cylindrical body portion of the tampon at any side or level to be absorbed internally thereof and by capillary action flow up to the top of the tampon which thereafter opens or flowers to further enhance the absorption characteristics of the tampon.

BRIEF DESCRIPTION OF THE DRAWINGS

Various other objects, advantages, and features of the invention will become apparent to those skilled in the art from the following discussion taken in conjunction with the following drawings, in which:

FIG. 3b is the wad of cotton of FIG. 2 folded to the side thereof opposite to the folding shown in FIG. 3a;

FIG. 13 is an isometric view of yet another embodiment of the inventive tampon illustrating folding the bottom portion onto itself prior to compression of the tampon into a cylindrical shape;

FIG. 14 is an isometric view of the bottom portion of the embodiment of FIG. 13 prior to folding, illustrating a groove therein for location of a pull string;

FIG. 15 is an isometric view of the reverse side of the bottom portion of the embodiment of FIG. 13 prior to folding, illustrating a string locating groove in the reverse side thereof;

FIG. 16 is a bottom view of the embodiment of FIG. 13 taken along the line 16—16 of FIG. 15;

FIG. 17 is an isometric view of another embodiment of the inventive tampon of FIG. 13 illustrating another method of folding the bottom portion prior to compression of the tampon into a cylindrical shape;

FIG. 18 is an isometric view of another embodiment of the tampon of FIG. 14 illustrating a once-folded-over configuration of the bottom portion thereof; and, FIG. 19 is yet another embodiment of the inventive tampon illustrating a single bottom fold in conjunction with an overlapping top fold.

DESCRIPTION OF THE PREFERRED EMBODIMENTS

Figure 1:
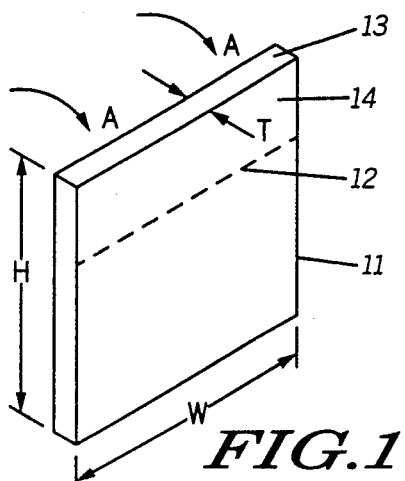
FIG. 1 is an isometric view of a wad of cotton material in sheet form before being formed into the cylindrical shape of a tampon.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

Figure 2:
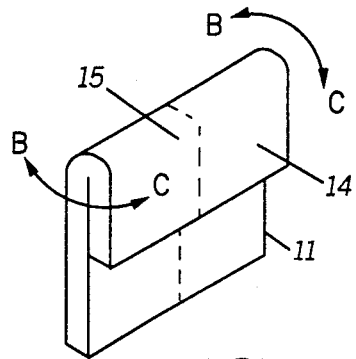
FIG. 2 is the wad of cotton of FIG. 1 with the top portion thereof folded downward.

Referring now to FIGS. 1 through 3 of the drawings, there is shown a wad of cotton or rayon or other like absorbent material 11 formed into a rectangular configuration having an appropriate thickness. Typically, the wad of cotton 11, before folding, may be of the size two inches wide by four and one-half inches high with a thickness of approximately one-quarter of an inch. In the forming of the inventive tampon 10, the upper portion of the rectangularly-shaped wad of cotton 11 is folded down over itself as indicated by the arrows A—A such that the configuration of FIG. 2 results therefrom. The upper portion 14 of the wad of cotton 11 may be folded along a horizontal line 12 such that the vertical distance between the horizontal line 12 and the upper edge 13 of wad 11 is approximately one-third of the height dimension of four and one-half inches, or one and one-half inches.

The once-folded-over wad of cotton 11, as shown in FIG. 2, is thereafter folded lengthwise along a vertical line 15, which vertical line 15 lies in the center of the width W of the wad of cotton 11. The once-folded-over wad of cotton 11 may be folded over in either of the directions of arrows BB or CC so as to respectively result in the configuration shown in the FIGS. 3a and 3b. In either of the configurations of FIGS. 3a or 3b it is seen that the original wad of cotton 11 is twice as thick in the upper half thereof as compared to the lower half thereof. Further the approximate dimensions of the wad of cotton 11 which is twice folded over is approximately three inches high by one inch wide with the upper portion 16 thickness being approximately one inch and the lower portion 17 thickness being approximately one-half inch. Physically, twice as much of the absorbent material exists in the upper half 16 as compared to the lower half 17.

Figure 3A:
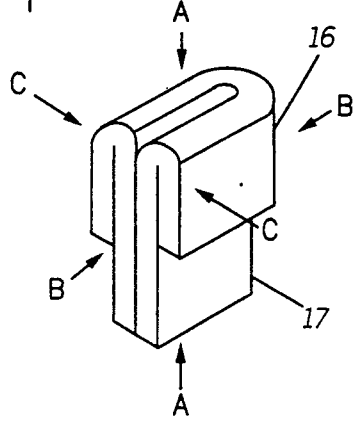
FIG. 3a is the wad of cotton of FIG. 2 being further folded to the side and along a longitudinal center axis.
Figure 3B:
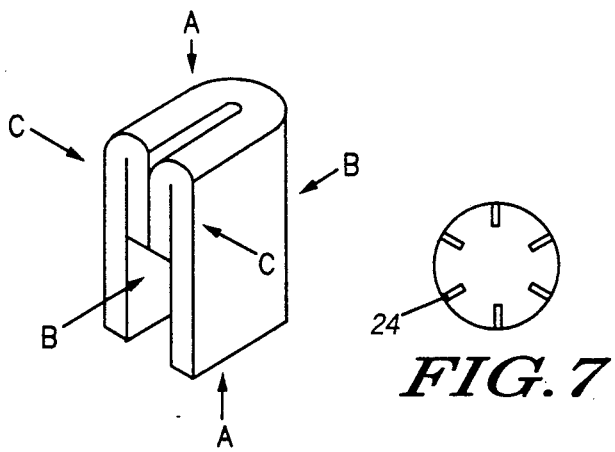
Figure 8:
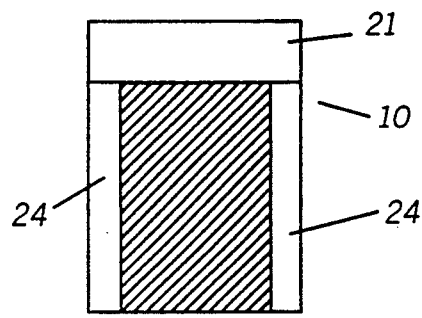
FIG. 8 is a cross-sectional view taken along the line 8—8 of FIG. 5.

Reference is now made to FIGS. 4 through 8 and FIG. 9 of the drawings. The twice-folded-over configuration of the wad of cotton 11 shown in FIGS. 3a or 3b is then subjected to compression along the planes indicated by arrows A, B and C. Such pressure may be exerted by a split mold having an internal configuration of a cylinder such as that shown in FIG. 4, the cylinder having a height of approximately two inches and a diameter of approximately five-eights of an inch. The top surface 18 may have a flat shape, a convex shape, or a concave shape. During or subsequent to the compression of the configuration shown in FIGS. 3a and 3b, a convenience cord 19 may be attached to the tampon 10 at the bottom 20 thereof.

Figure 4:
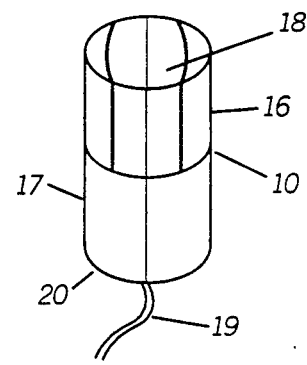
FIG. 4 illustrates the cylindrical shape of the wad of cotton of FIG. 3a or FIG. 3b after being subjected to a molding pressure.
Figure 5:
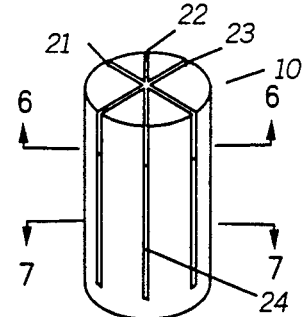
FIG. 5 illustrates the various slots and grooves provided in the cylindrical shape of the tampon.
Figure 7:
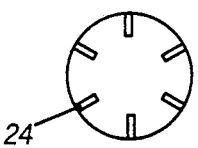
FIG. 7 is a cross-sectional view taken along the line 7—7 of FIG. 5.
Figure 6:
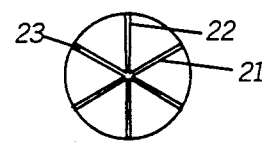
FIG. 6 is a cross-sectional view taken along the line 6—6 of FIG. 5.

Subsequent to the forming of the cylindrical shape shown in FIG. 4, the tampon 10 is slit in a plurality of diametrical locations across the upper portion 16 thereof to a depth of approximately one-half to two-thirds of the height of the upper portion 16. In the example shown in FIG. 5 a total of three slits 21, 22, and 23 are machined along three equally distant diameters of the circular cross-sectional shape of the inventive tampon 10. FIG. 6 illustrates in cross section the location of slits 21, 22, and 23. Further, a plurality of grooves 24 are provided in the cylindrical surface of the tampon 10 along the length thereof. Grooves 24 may be located at the same radially location of slits 21, 22, and 23 such that grooves 24 comprise a longitudinal extension of said slits. FIG. 7 illustrates, in cross section, a view of the grooves 24 in relation to the circular cross section of the tampon 10 at the bottom 17 thereof.

Slits 21, 22, and 23 and grooves 24 serve to allow menstrual fluid to be absorbed by the tampon 10 and to penetrate into the interior of the tampon and thereby provide for improved absorbent qualities thereof.

The new construction of the tampon 10, shown and described above, specifically takes into account the faulty positioning of the tampon within the vaginal canal. Thus, if the tampon is positioned too high in the vaginal canal such that the top 18 of the tampon is positioned past the os of the cervix, and is positioned behind the cervix in one of the fornices behind and to the side of the cervix, the menstrual fluid strikes the cylindrical side of a tampon 10 at the location of grooves 24. Grooves 24 allow the menstrual fluid to be directed toward and absorbed by the interior of the tampon and directs the menstrual fluid upwardly to the slitted portion of the tampon 10 because twice the absorptive capacity, and, therefore, twice the capillary action of the upper portion 16 as compared to the lower portion 17 as shown by the arrows "x" in FIG. 4. Slits 21, 22, and 23 thereafter allow the menstrual fluid to flow completely within the interior shape of the tampon 10. The flow of the menstrual fluid to the slitted area of the tampon 10 provides for opening up of or flowering of the upper portion 16 by resisting the contractile forces of the vaginal wall, which is a feature missing in all of the prior art tampons. By resisting the contractile action of the vaginal wall, the tampon 10 permits itself to expand and properly adapt itself to the vaginal contour (see FIG. 9), and also provide for maximum absorptive capacity to the tampon 10.

As previously stated, the completed tampon 10 may have a concave, convex, or flat top 18. Simple tests have shown that there is greater absorptive efficiency with a star-grooved flat top such as the slits 21, 22, and 23 shown in FIG. 6, as well as permitting more effective expansion and flowering at the top portion 16 thereof.

The separate pie-shaped sections at the top 18 of the tampon 10 as provided by slits 21, 22, and 23, flower out when either the top or the sides of the tampon 10 are exposed to the menstrual fluid. Accordingly, when the tampon 10 is properly placed within the vaginal canal such that the top surface 18 of the tampon 10 is more or less directly exposed to the flow of menstrual fluid, the more effective expansion and flowering at the top of the tampon 16 provided by the inventive tampon 10, readily absorbs the menstrual fluid. The mechanism of expansion and opening or separation of the folded parts of the tampon 10 is based upon wetness and saturation, which by swelling causes the absorptive parts to move further outwardly as they continue to swell and unfold. It is the swelling and associated outward unfolding that helps the tampon 10 resist the muscular contractile forces of the vaginal wall. Additional expansion of the tampon 10 occurs when the longitudinal fold (see FIGS. 3a and 3b) starts to open or unfold, thereby further enlarging the diameter of the tampon, which at the same time is creating a central space within the interior thereof to catch and hold blood clots. The flowering effect at the upper end 16 of the tampon 10 and the unfolding of the longitudinal fold, are positive and not passive actions or forces which resist the contractile forces of the vaginal musculature. The unfolding and flowering effect of the tampon 10 also assists the tampon 10 in adapting itself to the size, contour, and oblique plane of the vaginal canal.

The grooves 24, which are circumferentially spaced and aligned with the slits 21, 22, and 23, serve to rapidly absorb the menstrual fluid striking the side of the tampon, and guide the menstrual fluid inwardly (toward the center) and downwardly, whether the tampon is properly or improperly positioned; the said grooves continue to assist in absorption even as the menstrual fluid continues to flow downwardly.

Figure 10:
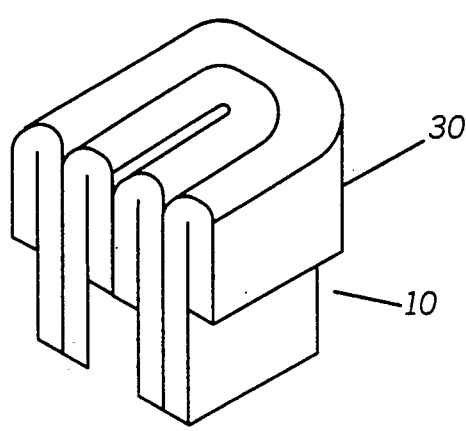
FIG. 10 is an isometric view of another method to fold the wad of material prior to being compressed into a cylindrical shape.
Figure 9:
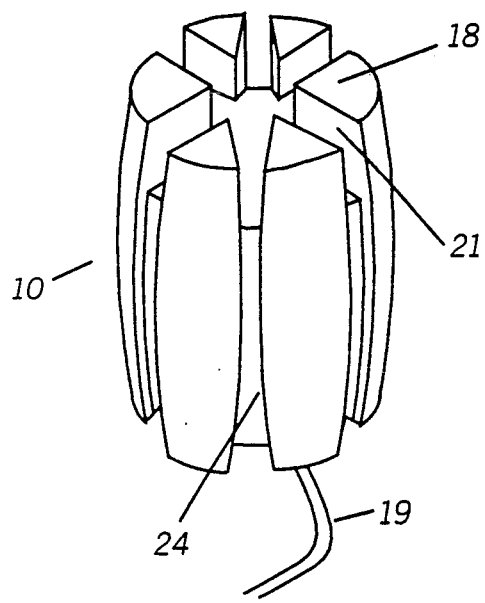
FIG. 9 is a schematic rendering of the inventive tampon after it has been used to absorb a fluid.

The folded example 30 of the tampon 10 shown in FIG. 10 is yet another way to fold the wad of cotton 11 prior to it being compressed into a cylindrical shape. As can be seen in FIG. 10, the folded wad of cotton 30 has eight thicknesses at the top and four thicknesses at the bottom.

Figure 12:
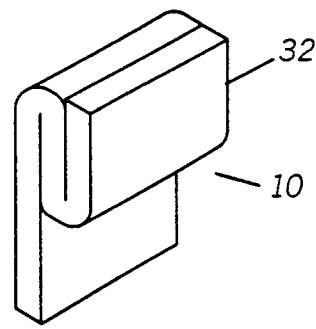
FIG. 12 is an isometric view of still another method to prepare a piece of absorptive material prior to being compressed into a cylinder.
Figure 11:
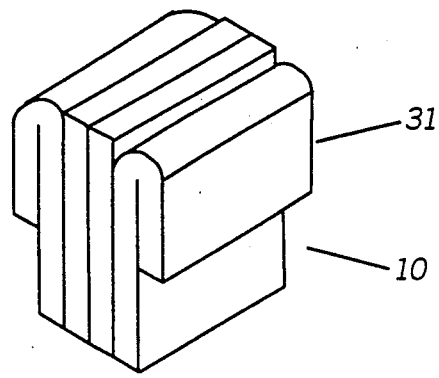
FIG. 11 is an isometric view of yet another method to prepare pieces of absorptive material prior to being compressed into a cylindrical shape.

The folded and pieced together wad of absorptive material 31 shown in FIG. 11 is yet another way to prepare one or more pieces of material prior to being compressed into a cylindrical shape. In this example, there are approximately six thicknesses of material at the top and four at the bottom. Another example, FIG. 12, shows as much as three times the thickness at the top as compared to the bottom portion.

FIGS. 13 through 19 show other embodiments of the inventive tampon before compression into a cylindrical shape, wherein the bottom portion thereof is folded so as to cause the pull string 19 to be located within the folded-over portion so that after insertion of the tampon string 19 may be pulled down to unfold the folded-over bottom portion of the tampon prior to being used to absorb the menstrual fluid. After insertion and after being unfolded, the unfolded bottom portion of the tampon by the action of pulling the pull string downward is physically uncompressed so as to better allow the natural absorptive characteristics of the tampon to act in its intended capacity. Also, when folded down, the previous cylindrical shape of the tampon tends to assume a flattened shape which better fits the natural shape of the vaginal cavity and thereby provides for even better absorption, lessens by-passing, and provides more comfort for the user.

In the embodiment of FIG. 13, in the inventive tampon 40, includes an upper portion 41 and a lower portion 42, each of which may be folded over upon itself as shown in FIG. 13. In FIG. 13 the upper portion 41 is folded over onto itself such that the folded-over portion 46 folds down once upon itself. However, the folded-over upper portions shown in FIGS. 1 through 12 of the previous embodiments may also be applied to this embodiment.

The bottom 42 folded-over portion of the tampon 40 of FIG. 13 illustrates a triple folded-over portion 42, such that portion 43 is folded over against portion 44 before both portions 43 and 44 are together folded in the same direction over the portion 53 of tampon 40. The folded-over arrangement shown in FIG. 13 is accomplished prior to the compressive pressures in the direction of arrows A, B and C are applied to the uncompressed piece or wad of cotton or other absorptive material prior to the same being compressed into, for example, a cylindrical shape as shown in FIG. 4 of the drawings.

To explain and further describe the location and action of the pull or drawstring 19 which is also folded over when bottom portion 42 of tampon 40 is folded over onto itself as shown in FIG. 13, reference is now made to FIGS. 14 through 16 of the drawings. FIG. 14 illustrates the bottom portion 42 of a uncompressed piece or wad or absorptive material 11 having the pull string 19 wrapped around the girth thereof and exiting through a hole 47 through the thickness of the bottom portion 42 of the uncompressed piece of absorptive material 11. Upon exiting from hole 47, both of the strands of pull string 19 lies within a slit or groove 48 extending longitudinally from hole 47 to the bottom surface 51 of the piece of absorptive material 11. The reverse side of the bottom portion 42 of the uncompressed piece of absorptive material 11 is shown in FIG. 15. Here it is seen that a slit or groove 49 extends also from the opening 47 downward to the bottom face 51 while slit or groove 45 extends upward in a longitudinal manner from opening 47. Slits 48, 49, and 45 are cut sufficiently deep so as to substantially encompass and provide a groove for both strands of pull string 19. Accordingly, slit 48, 49, and 45 should not be through the full thickness of the uncompressed piece of absorptive material 11. FIG. 16 shows yet another slit 50 cut into the bottom face 51.

FIG. 14 illustrates the unfolded position of the bottom portion 42 of the inventive tampon 40 prior to being folded over as shown in FIG. 13. In constructing the embodiment of FIG. 13, the portion 43 containing the transverse position of pull string 19 is folded up and against the face 52 of portion 44 above the transverse location of pull string 19. Then, portions 43 and 44 are together folded in the same direction about an imaginary line designated numbered 55 in FIG. 14. The resulting shape is that shown in FIG. 13. During this folding-over procedure, string 19 is caused to stay within the confines of slits 48, 50, 49, and then 45 in the order thereof as stated. The final configuration is such that both strands of pull string 19 are fitted within slit 45 prior to the absorptive piece of material 11 being compressed into a cylindrical shape. Slits 48, 50, 49, and 45 are beneficial to the locating of pull string 19 but are not an essential requirement. the folded-over configuration of FIG. 13 is then subjected to external pressure so as to form the same into a cylindrical or other appropriate shape.

FIG. 17 shows yet another embodiment of the folded-over bottom portion 42 of the uncompressed piece of absorptive material 11. In this embodiment, folded-over portion 43 is folded over and against 44 both of which are then folded over against portion 53 in an accordion type of fold. Both strands of drawstring 19 are, in this embodiment, may be fitted only within a slit 48. Then, the uncompressed absorptive piece of material 11 is subjected to the pressures depicted by arrows A, B and C such as to form the tampon 40 into a cylindrical or other appropriate shape.

In the configuration of FIG. 18, the bottom portion 42 comprises a once-folded-over portion 43. The longitudinal length of portion 43 may extend from bottom face 51 to a distance beyond the transverse location of pull string 19. Such length may be variable depending upon the length of unfolding desired.

In the embodiment of FIG. 19, the upper folded-over portion 46 of upper portion 41 overlaps the upper part of folded-over portion 43 of the bottom portion 42 prior to being compressed into an appropriate shape. In this manner, when the dry tampon is inserted and pull string 19 is pulled downward to unfold bottom portion 42, the overlapping part 56 of folded-over portion 46 is partially relived of its cylindrical or other appropriate shape compressing force so as to lift it away from the compressed upper portion 41 and thereby allow the upper portion 41 to better absorb menstrual fluids.

After being formed into a cylindrical or other appropriate shape, the embodiments of FIGS. 13 through 19 may then be inserted within a vaginal canal with, of course, the drawstring 19 being in a lowermost position within the canal. Once the tampon 40 is inserted to its appropriate depth, pull string 19 is then pulled with only that sufficient force so as to cause the unfolding of the lower portion 42 into a lower position within the vaginal canal. At this time, portion 43 will be at the lowermost position, with portion 44 being located immediately thereabove and with portion 53 being located above portion 44, all of which are below upper portion 41. The unfolding of the folded-over portions 43 or 43 and 44, has the reverse effect of the compression applied to the tampon in order to form it into a cylindrical or other appropriate shape. This physical uncompressing action of the dry tampon by gently pulling on pull string 19 allows the bottom portion 42 of tampon 40 to be substantially improved as to its absorbing capabilities and shape within the vaginal canal as compared to a fully compressed tampon having no folds at this location.

While the upper portion of tampon 40, as shown in FIG. 3, reflects a once-folded-over configuration as explained above, any of the folded-over configurations shown in FIGS. 1 through 12 of the drawings apply equally as well to the embodiment of the tampon 40 of FIG. 13. Also, the axial slits placed in the upper portion of a compressed and cylindrically-shaped tampon such as that shown in FIG. 5 of the drawings, may equally be applied to the embodiment of FIG. 13.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the scope of the breadth and scope of the claims here appended.

I claim as my invention:

1. A method of manufacturing a tampon adapted for absorbing menstrual fluids and being placed within a vaginal canal comprising the steps of folding a top portion of a rectangularly-shaped piece of absorbing material over a horizontal line and down along a side thereof folding said once-folded rectangularly-shaped piece of material along a vertical line such that the resulting shape comprises a twice-folded piece of material having double the thickness at the top thereof compared to the bottom thereof applying pressure to said twice-folded piece of material to form said piece of material into a solid, cylindrical shape.

2. The method of claim 1, including the step of inserting one or more pieces of absorbing material between said twice-folded piece of material.

3. The method of claim 1, including the step of slitting the upper portion of said cylindrical shaped piece of material along one or more planes coincident with the longitudinal axis of said cylindrical shape.

4. The method of claim 3, including the step of grooving the cylindrical surface of said cylindrical shape along longitudinal lines aligned with said one or more slits.

5. A tampon adapted to be inserted within a vaginal canal for absorption of menstrual fluid comprising one or more pieces of absorptive material formed into an elongated member having a lower portion thereof transversely folded over upon itself one or more times a pull string being attached to said one or more pieces of absorptive material and being positioned such that it extends from an upper end of the folded-over lower portion and downward longitudinally along an outside face of the folded-over lower portion to and past a lower end of the tampon said one or more pieces of absorptive material including the folded over lower portion being longitudinally shaped as an approximate cylinder.

6. The tampon construction of claim 5, further comprising a groove provided in the surface of said one or more pieces of absorptive material for substantially fixing the longitudinal location of said drawstring.

7. The tampon of claim 5, wherein said lower portion is transversely folded over twice upon itself in an accordion type of fold.

8. The tampon of claim 7, wherein said pull string extending down from the end portion of said tampon fits within an longitudinal groove formed in the surface of said tampon, said groove extending from the location of the pull string being attached to said tampon to approximately the lower end of said tampon.

9. The tampon of claim 5, wherein said folded-over lower portion comprises a double folded-over portion with a first fold transversely folded upon itself, and a second fold comprising the once folded-over lower portion being again transversely folded upon itself.

10. The tampon of claim 9, further comprising a longitudinally extending groove formed into the surface of one of said one or more pieces of absorptive material for fixing the longitudinal location of said pull string.

11. The tampon of claim 5, including an upper portion folded over upon itself one or more times.

12. The tampon of claim 11, wherein said folded-over upper portion overlaps said folded-over lower portion whereby pulling of said pull string causes said overlapping folded-over upper portion to lift away from the upper portion of said tampon.

13. A method of manufacturing a tampon comprising an elongated member adapted to be inserted within a vaginal canal for absorption of menstrual fluids, comprising attaching a pull string to one or more pieces of absorptive material such that it extends from a first end thereof transversely folding over a first end portion having said first end included therewith and having the pull string extending therefrom over onto itself such that the pull string extends longitudinally from said first end of said folded over first end portion down to a lower end of said folded-over first end portion applying pressure to said one or more pieces of absorptive material forming an approximate cylindrical shape.

14. The method of claim 13, including the step of folding over a second end portion not having the pull string extending thereto over upon itself.

15. The method of claim 14, including the step of overlapping said second end portion over said first end portion.

16. The method of claim 13, including the step of twice folding over said first end portion.

* * * * *